(12) United States Patent
Mirsepassi et al.

(10) Patent No.: US 11,173,008 B2
(45) Date of Patent: Nov. 16, 2021

(54) ILLUMINATED OPHTHALMIC CANNULA

(71) Applicant: Novartis AG, Basel (CH)

(72) Inventors: Alireza Mirsepassi, Irvine, CA (US);
Michael James Papac, North Tustin, CA (US); Barry L. Wheatley, Oceanside, CA (US); Chenguang Diao, Irvine, CA (US)

(73) Assignee: Alcon Inc., Fribourg (CH)

( * ) Notice: Subject to any disclaimer, the term of this patent is extended or adjusted under 35 U.S.C. 154(b) by 655 days.

(21) Appl. No.: 15/073,878

(22) Filed: Mar. 18, 2016

(65) Prior Publication Data

US 2017/0119491 A1    May 4, 2017

Related U.S. Application Data

(60) Provisional application No. 62/249,313, filed on Nov. 1, 2015.

(51) Int. Cl.
| | |
|---|---|
| *A61B 90/30* | (2016.01) |
| *A61F 9/007* | (2006.01) |
| *A61B 1/07* | (2006.01) |
| *A61B 1/32* | (2006.01) |

(52) U.S. Cl.
CPC ............ *A61B 90/30* (2016.02); *A61B 1/07* (2013.01); *A61B 1/32* (2013.01); *A61F 9/007* (2013.01); *A61B 2090/306* (2016.02)

(58) Field of Classification Search
CPC .......... A61F 9/007; A61B 90/30; A61B 1/07; A61B 1/32; A61B 2090/306
USPC ................... 606/4–6; 600/184–249
See application file for complete search history.

(56) References Cited

U.S. PATENT DOCUMENTS

| | | | |
|---|---|---|---|
| 3,089,484 A | 5/1963 | Hett | |
| 3,093,134 A | 6/1963 | Roehr | |
| 3,131,690 A | 5/1964 | Innis et al. | |
| 3,385,553 A | 5/1968 | Braun | |
| 3,439,157 A | 4/1969 | Myles | |
| 3,910,677 A | 10/1975 | Becker et al. | |
| 3,932,022 A | 1/1976 | Henning et al. | |

(Continued)

FOREIGN PATENT DOCUMENTS

| | | |
|---|---|---|
| DE | 19957785 | 6/2000 |
| EP | 0684016 | 11/1995 |

(Continued)

OTHER PUBLICATIONS

International Searching Authority, Search Report and WO of the International Searching Authority, PCT/US2011/046942, dated Nov. 3, 2011, 4 pages.

(Continued)

*Primary Examiner* — Matthew J Lawson

(57) ABSTRACT

An ophthalmic cannula assembly may include a cannula having an outer cannula surface and an inner cylindrical bore. A hub adjoining a proximal end of the cannula may define a maximum outer hub diameter that is greater than an outer diameter of the cannula. An optical fiber may be attached to the outer cannula surface for at least a portion of a length of the cannula. A cover material may be in contact with the outer cannula surface, and may cover at least a portion of the optical fiber. A light diffuser may be disposed at a distal tip of the optical fiber.

20 Claims, 16 Drawing Sheets

(56) References Cited

U.S. PATENT DOCUMENTS

| | | | |
|---|---|---|---|
| 3,981,709 A | 9/1976 | Kondo et al. | |
| 3,990,453 A | 11/1976 | Douvas et al. | |
| 4,168,707 A | 9/1979 | Douvas et al. | |
| 4,200,106 A | 4/1980 | Douvas et al. | |
| 4,551,129 A | 11/1985 | Coleman et al. | |
| 4,597,030 A | 6/1986 | Brody | |
| 4,607,622 A | 8/1986 | Fritch et al. | |
| 4,641,912 A | 2/1987 | Goldenberg | |
| 4,678,268 A | 7/1987 | Russo et al. | |
| 4,693,244 A | 9/1987 | Daikuzono | |
| 4,693,556 A | 9/1987 | McCaughan, Jr. | |
| 4,733,933 A | 3/1988 | Pikulski | |
| 4,781,703 A | 11/1988 | Walker et al. | |
| 4,842,390 A | 6/1989 | Sottini et al. | |
| 4,872,837 A | 10/1989 | Issalene et al. | |
| 4,994,047 A | 2/1991 | Walker et al. | |
| 4,995,691 A | 2/1991 | Purcell, Jr. | |
| 5,037,174 A | 8/1991 | Thompson | |
| 5,201,730 A | 4/1993 | Easley et al. | |
| 5,217,456 A | 6/1993 | Narciso, Jr. | |
| 5,219,350 A | 6/1993 | Emerson et al. | |
| 5,263,952 A | 11/1993 | Grace et al. | |
| 5,275,593 A | 1/1994 | Easley et al. | |
| 5,312,393 A | 5/1994 | Mastel | |
| 5,351,168 A | 9/1994 | Easley | |
| 5,411,016 A | 5/1995 | Kume et al. | |
| 5,425,730 A | 6/1995 | Luloh | |
| 5,478,338 A | 12/1995 | Reynard | |
| 5,591,160 A | 1/1997 | Reynard | |
| 5,620,639 A | 4/1997 | Stevens et al. | |
| 5,630,809 A | 5/1997 | Connor | |
| 5,632,740 A | 5/1997 | Koch et al. | |
| 5,651,783 A | 7/1997 | Reynard | |
| 5,667,472 A | 9/1997 | Finn et al. | |
| 5,695,492 A | 12/1997 | Brown | |
| 5,716,320 A | 2/1998 | Buttermore | |
| 5,725,514 A | 3/1998 | Grinblat et al. | |
| 5,754,717 A | 5/1998 | Esch | |
| 5,860,996 A | 1/1999 | Urban et al. | |
| 5,916,149 A * | 6/1999 | Ryan, Jr. | A61B 5/0059 362/344 |
| 6,080,143 A | 6/2000 | Connor | |
| 6,206,823 B1 | 3/2001 | Kolata et al. | |
| 6,217,456 B1 | 4/2001 | Jacob | |
| 6,387,044 B1 | 5/2002 | Tachibana et al. | |
| 6,428,553 B1 | 8/2002 | Trese | |
| 6,454,744 B1 | 9/2002 | Spohn et al. | |
| 6,939,341 B2 | 9/2005 | Vijfvinkel | |
| 7,473,249 B2 | 1/2009 | Scheller et al. | |
| 7,492,987 B2 * | 2/2009 | Yeik | A61B 18/24 385/31 |
| 7,593,778 B2 * | 9/2009 | Chandran | A61B 18/1477 607/116 |
| 7,766,904 B2 | 8/2010 | McGowan, Sr. et al. | |
| 7,783,346 B2 | 8/2010 | Smith et al. | |
| 7,881,573 B2 | 2/2011 | Eberle et al. | |
| 7,896,838 B2 | 3/2011 | Devega | |
| 7,901,353 B2 | 3/2011 | Vayser et al. | |
| 8,496,862 B2 | 7/2013 | Zelkovich et al. | |
| 8,900,139 B2 | 12/2014 | Yadlowsky et al. | |
| 8,968,347 B2 | 3/2015 | McCollam | |
| 9,055,885 B2 | 6/2015 | Horvath et al. | |
| 9,066,678 B2 | 6/2015 | Auld et al. | |
| 9,089,364 B2 | 7/2015 | Bhadri et al. | |
| 9,364,982 B2 | 6/2016 | Schaller | |
| 9,402,643 B2 | 8/2016 | Auld et al. | |
| 9,561,085 B2 | 2/2017 | Yadlowsky et al. | |
| 9,839,749 B2 | 12/2017 | Johnson et al. | |
| 9,956,053 B2 | 5/2018 | Diao et al. | |
| 10,016,248 B2 | 7/2018 | Mirsepassi et al. | |
| 10,039,669 B2 | 8/2018 | Heeren | |
| 2001/0056278 A1 | 12/2001 | Nield et al. | |
| 2002/0035425 A1 | 3/2002 | Deguchi et al. | |
| 2002/0123744 A1 | 9/2002 | Reynard | |
| 2004/0215065 A1 | 10/2004 | Setten | |
| 2005/0080384 A1 | 4/2005 | Green, Jr. | |
| 2005/0135776 A1 | 6/2005 | Vijfvinkel | |
| 2005/0154379 A1 | 7/2005 | McGowan, Sr. et al. | |
| 2005/0245916 A1 | 11/2005 | Connor | |
| 2006/0135973 A1 | 6/2006 | Hawkins et al. | |
| 2006/0211918 A1 | 9/2006 | Lieponis | |
| 2007/0179430 A1 | 8/2007 | Smith et al. | |
| 2007/0255264 A1 | 11/2007 | Hickingbotham | |
| 2008/0108981 A1 | 5/2008 | Telfair et al. | |
| 2008/0147018 A1 | 6/2008 | Squilla et al. | |
| 2008/0179792 A1 | 7/2008 | Kurimoto et al. | |
| 2008/0255545 A1 | 10/2008 | Mansfield et al. | |
| 2009/0030406 A1 | 1/2009 | Hickingbotham | |
| 2009/0131931 A1 | 5/2009 | Lee et al. | |
| 2009/0135280 A1 | 5/2009 | Johnston et al. | |
| 2009/0161384 A1 | 6/2009 | Smith | |
| 2009/0163897 A1 | 6/2009 | Skinner | |
| 2009/0182313 A1 | 7/2009 | Auld et al. | |
| 2009/0221991 A1 | 9/2009 | Lieponis | |
| 2010/0026207 A1 | 2/2010 | Facchini et al. | |
| 2010/0081875 A1 | 4/2010 | Fowler et al. | |
| 2010/0145284 A1 | 6/2010 | Togashi | |
| 2010/0228083 A1 | 9/2010 | Mirza et al. | |
| 2010/0228085 A1 | 9/2010 | Mirza et al. | |
| 2011/0130779 A1 | 6/2011 | Mirza et al. | |
| 2011/0282160 A1 * | 11/2011 | Bhadri | A61B 3/0008 600/236 |
| 2011/0319839 A1 | 12/2011 | Del Vecchio | |
| 2012/0035425 A1 * | 2/2012 | Schaller | A61F 9/00736 600/249 |
| 2012/0041461 A1 | 2/2012 | McCollam | |
| 2012/0203075 A1 | 8/2012 | Horvath | |
| 2012/0238830 A1 | 9/2012 | Vukeljic et al. | |
| 2012/0283523 A1 | 11/2012 | Yadlowsky et al. | |
| 2012/0296173 A1 | 11/2012 | Stocks et al. | |
| 2013/0012783 A1 | 1/2013 | Vayser et al. | |
| 2013/0079598 A1 * | 3/2013 | Auld | A61B 3/0008 600/249 |
| 2013/0267786 A1 * | 10/2013 | Vayser | A61B 1/32 600/205 |
| 2013/0282031 A1 | 10/2013 | Woodard, Jr. et al. | |
| 2014/0100426 A1 | 4/2014 | Barbour | |
| 2014/0107630 A1 * | 4/2014 | Yeik | G02B 6/001 606/5 |
| 2014/0121469 A1 | 5/2014 | Mccollam et al. | |
| 2014/0210116 A1 | 7/2014 | Schaller | |
| 2014/0357957 A1 | 12/2014 | Bhadri et al. | |
| 2014/0379054 A1 | 12/2014 | Cooper et al. | |
| 2015/0011838 A1 | 1/2015 | Auld et al. | |
| 2015/0011839 A1 | 1/2015 | Auld et al. | |
| 2016/0113722 A1 | 4/2016 | Heeren | |
| 2017/0014023 A1 | 1/2017 | Kern | |
| 2017/0014267 A1 | 1/2017 | Kern et al. | |
| 2017/0165114 A1 | 6/2017 | Hallen et al. | |
| 2018/0055596 A1 | 3/2018 | Johnson | |
| 2018/0132963 A1 | 5/2018 | Diao et al. | |
| 2018/0133057 A1 | 5/2018 | Diao et al. | |
| 2018/0168768 A1 | 6/2018 | Mirsepassi et al. | |
| 2018/0168861 A1 | 6/2018 | Mirsepassi et al. | |
| 2018/0338776 A1 | 11/2018 | Farley et al. | |
| 2018/0338859 A1 | 11/2018 | Mirsepassi et al. | |
| 2019/0307527 A1 * | 10/2019 | Grueebler | A61B 90/30 |
| 2021/0128356 A1 * | 5/2021 | Moreno | A61F 9/00781 |

FOREIGN PATENT DOCUMENTS

| | | |
|---|---|---|
| GB | 1207229 | 9/1970 |
| GB | 1349881 | 4/1974 |
| JP | H10234665 | 9/1998 |
| JP | 2000245740 | 9/2000 |
| JP | 2001079010 | 3/2001 |
| JP | 2006325973 | 12/2006 |
| JP | 2009519766 | 5/2009 |
| JP | 2009148550 | 7/2009 |
| PL | 166358 | 5/1995 |
| WO | 0139705 | 6/2001 |
| WO | 0248017 | 6/2002 |
| WO | 2004002337 | 1/2004 |

(56) References Cited

FOREIGN PATENT DOCUMENTS

| WO | 2007081474 | 7/2007 |
|---|---|---|
| WO | 08139982 | 11/2008 |
| WO | 2008139982 | 11/2008 |
| WO | 2009091462 | 7/2009 |
| WO | 2012083247 A1 | 6/2012 |
| WO | 2015101624 A1 | 7/2015 |

OTHER PUBLICATIONS

European Search Report for Application No. 13851516.8, Publication No. EP2861125, Published Apr. 22, 2015, 6 pages.
International Search Report and Written Opinion, PCT/US2015/054426, dated Jan. 8, 2016, 15 pages.
International Search Report and Written Opinion of the International Searching Authority, International Application No. PCT/2013/067083, dated Jan. 16, 2014, 9 pages.
PCT International Preliminary Report on Patentability and Written Opinion, Application No. PCT/US2013/67083, Publication No. W0/2014/070664, dated May 5, 2015, 8 pages.
International Search Report for PCT/US2008/086119, Publication No. WO2009/091462, dated Mar. 30, 2009, 2 pages.
PCT International Preliminary Report on Patentability and Written Opinion of the International Searching Authority, International Application No. PCT/US2008/086119, dated Jul. 20, 2010, 7 pages.
PCT International Preliminary Report on Patentability and Written Opinion, PCT/US2011/046942, dated Feb. 12, 2013, 6 pages.
International Search Report for PCT/US2011/046942, dated Nov. 15, 2011, 4 pages.
International Search Report for PCT/US2011/047262, dated Dec. 12, 2011, 2 pages.
Supplementary European Search Report for PCT/US2011/047262, dated Oct. 9, 2013, 8 pages.
Calhoun, The Roto-Extractor in Pediatric Ophthalmology, Tr. Am. Ophth. Soc., vol. LXXIII, pp. 292-305, 1975.
Carron, Fiber Optics in Computer Screens to Save Energy, Feb. 22, 2012, 2 pages, retrieved Oct. 29, 2015 from http://phys.org/news/2012-02-fiber-optics-screens-energy.html.
Chalam, et al., Illuminated Curved Vitrectomy Probe for Vitreoretinal Surgery, Ophthalmic Surgery, Lasers and Imaging, Nov./Dec. 2007—vol. 38—Issue 6: 525-526.
Douvas, Microsurgical Roto-Extractor Instrument for Vitrectomy, Mod. Probl. Ophthal., vol. 15, pp. 253-260 (Karger, Basel 1975).
Fisher et al., Inexpensive Illuminated Vitrectomy Cutter, The Journal of Retinal and Vitreous Diseases, Dec. 2003, vol. 23, Issue 6, p. 891.
International Search Report and Written Opinion of the International Searching Authority, International Application No. PCT/IB2016/051993, not yet published, Jun. 16, 2016, 11 pages.

\* cited by examiner

ILLUMINATED OPHTHALMIC CANNULA

BACKGROUND

Microsurgical instruments may be used by surgeons for removal of tissue from delicate and restricted spaces in the human body. Ophthalmic surgical procedures involve manipulation of instruments in delicate and restricted spaces. These ophthalmic surgical procedures may include removal of the vitreous body, blood, scar tissue, or the crystalline lens. Such instruments may include a control console and a surgical hand piece with which the surgeon dissects and removes the tissue. A hand piece for ophthalmic posterior segment surgery may be a vitreous cutter probe, a laser probe, or an ultrasonic fragmenter for cutting or fragmenting the tissue (e.g., a phacoemulsification hand piece).

During ophthalmic posterior segment surgery, the surgeon may successively use different hand pieces or instruments. A surgical procedure may require that these instruments be inserted into and removed from an incision. Repeated removal and insertion of instruments may cause trauma to the eye at the incision site. To reduce such trauma, hubbed cannulae have been developed and used to help protect the incision site. These devices may include a narrow tube with an attached hub. The tube may be inserted into an incision in the eye up to the hub, which may act as a stop to prevent the tube from entering the eye completely. The hub may be stitched to the eye to prevent inadvertent removal.

Surgical instruments can be inserted into the eye through the cannula, and the cannula may protect the incision side wall from repeated contact by the instruments. In addition, the surgeon may manipulate and position the instrument within the eye through the cannula. The hub of the cannula may be designed to not protrude to an excessive height above the surface of the eye, and to control a loss of intraocular pressure during instrument exchange or removal. Otherwise, the eye, being a pressurized globe, may expel aqueous or vitreous through the open cannula when a surgical device is not present.

In many ophthalmic surgical procedures, more than one surgical instrument must be inserted into the eye simultaneously. For example, the surgeon may need to insert and position a light source to illuminate an interior region of the eye, while simultaneously inserting and positioning a surgical hand piece for cutting and aspirating tissue from the illuminated region. Another probe for providing irrigation fluid to maintain intraocular pressure during aspiration of cut tissue may also be simultaneously required to be inserted and positioned within the eye.

Therefore, it is common for several hubbed cannula to need to be inserted through the surface of the eye at different locations to simultaneously meet various requirements of an ophthalmic surgical procedure. Each incision point through the surface of the eye to accommodate an additional cannula is invasive and creates additional trauma to the eye, and therefore may increase the risk of infection or otherwise lengthen postoperative recovery.

DETAILED DESCRIPTION

Figure 1:
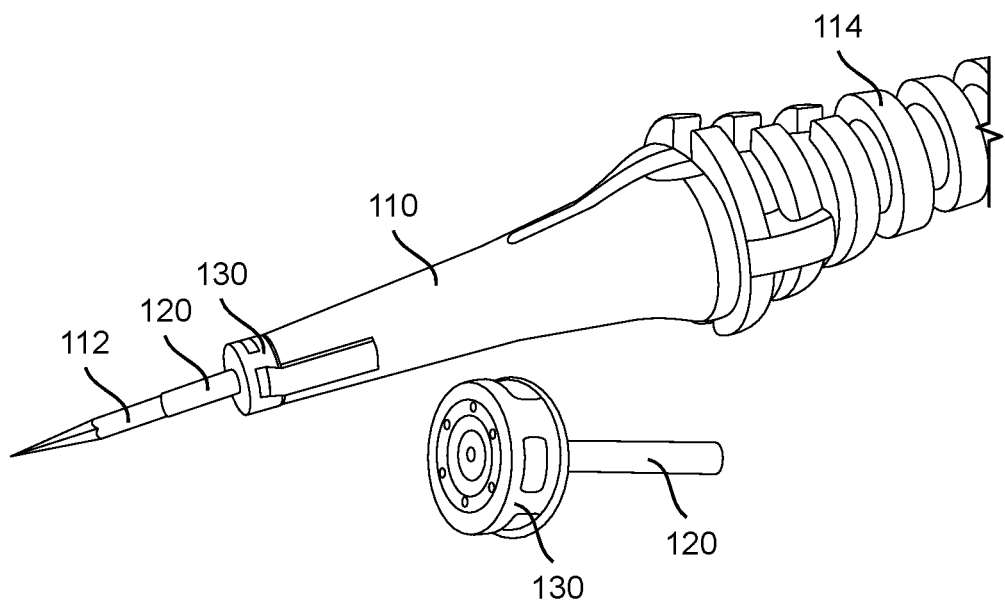
FIG. 1 depicts an example trocar piercing device and hubbed cannula for ophthalmic surgery.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Figure 2:
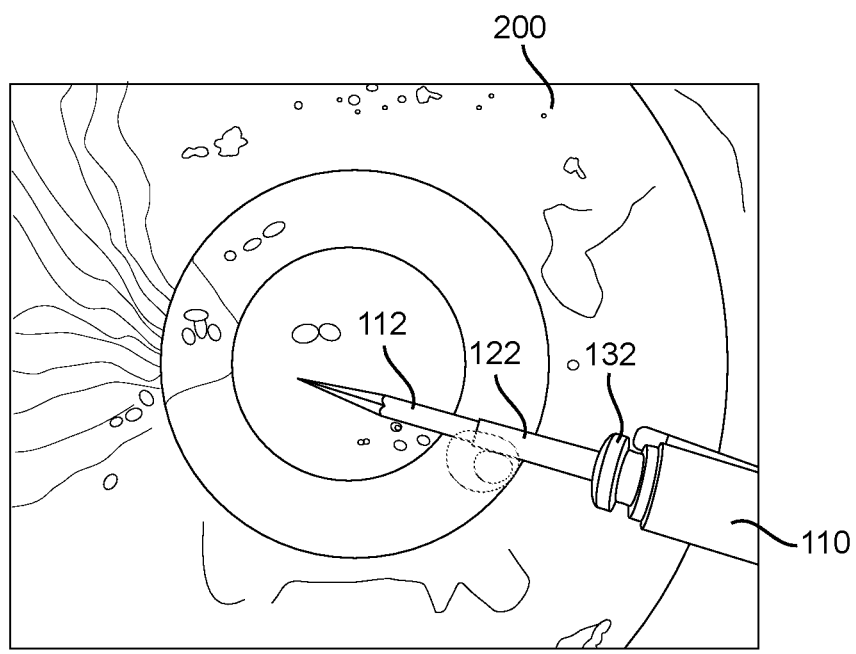
FIG. 2 depicts the insertion of an example trocar piercing device and hubbed cannula for ophthalmic surgery into the eye.

FIG. 1 depicts a trocar piercing device 110 and cannula 120 with hub 130 for ophthalmic surgery. The trocar piercing device 110 includes a trocar piercing lance 112 and a handle 114 for manipulation by a user, such as a surgeon or other medical professional. FIG. 2 depicts the use of the trocar piercing device 110 to insert the trocar piercing lance 112 and a cannula 122, with a hub 132, into a human eye 200.

Figure 3:
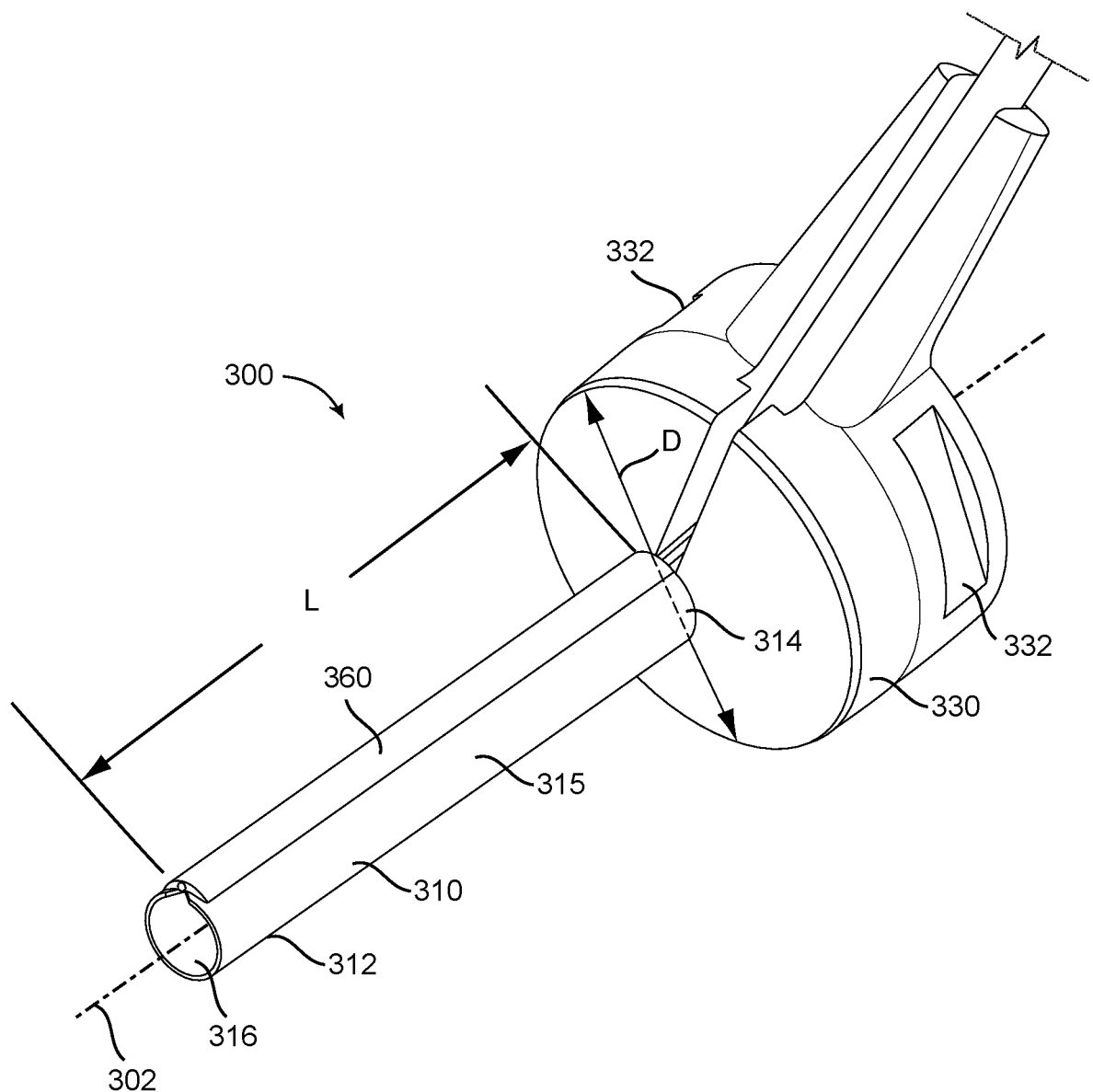
FIG. 3 depicts an example hubbed ophthalmic cannula assembly.
Figure 4:
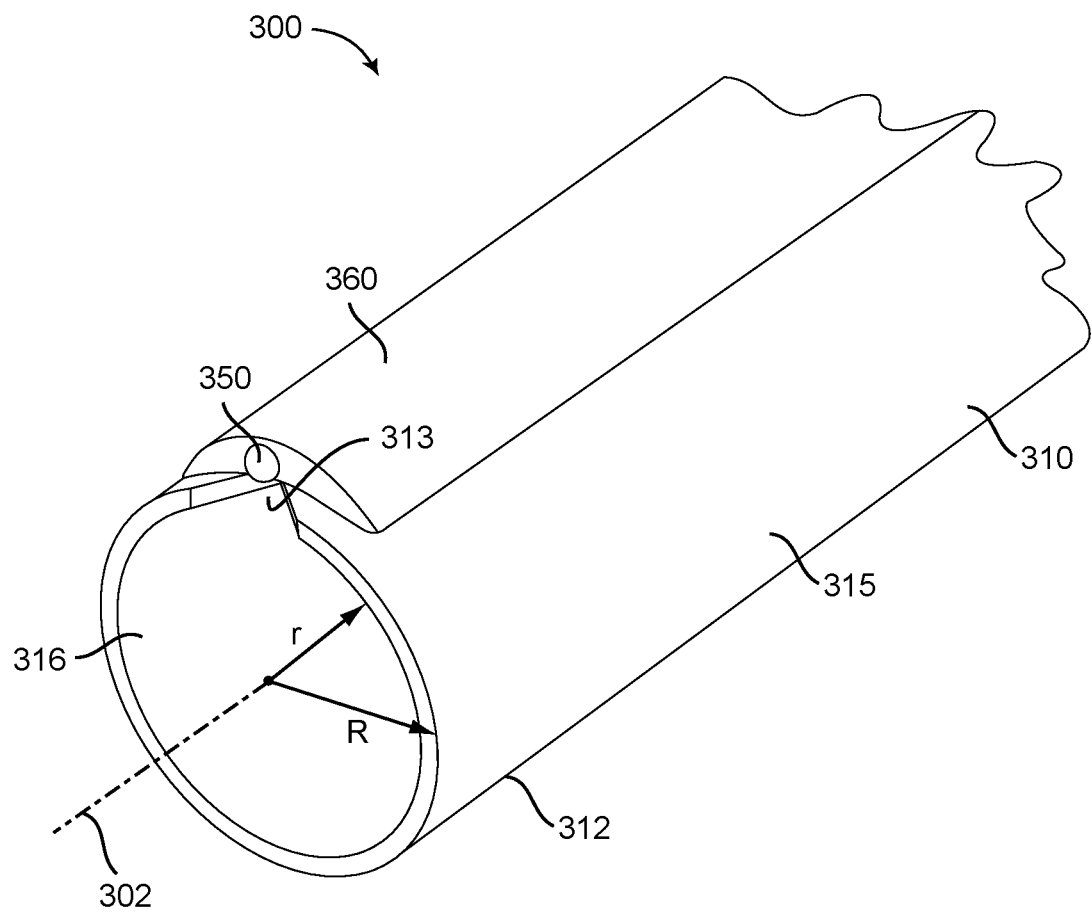
FIG. 4 is a perspective view of the distal end of the ophthalmic cannula assembly of FIG. 3.
Figure 5:
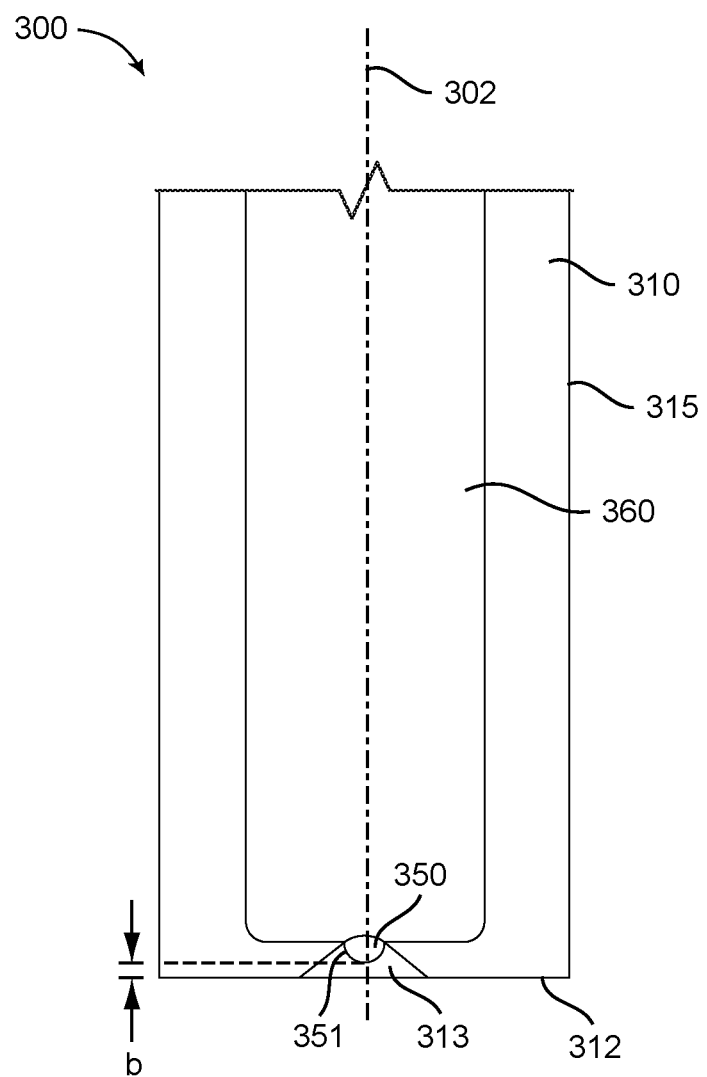
FIG. 5 is a plan view of the distal end of the ophthalmic cannula assembly of FIG. 3.
Figure 6:
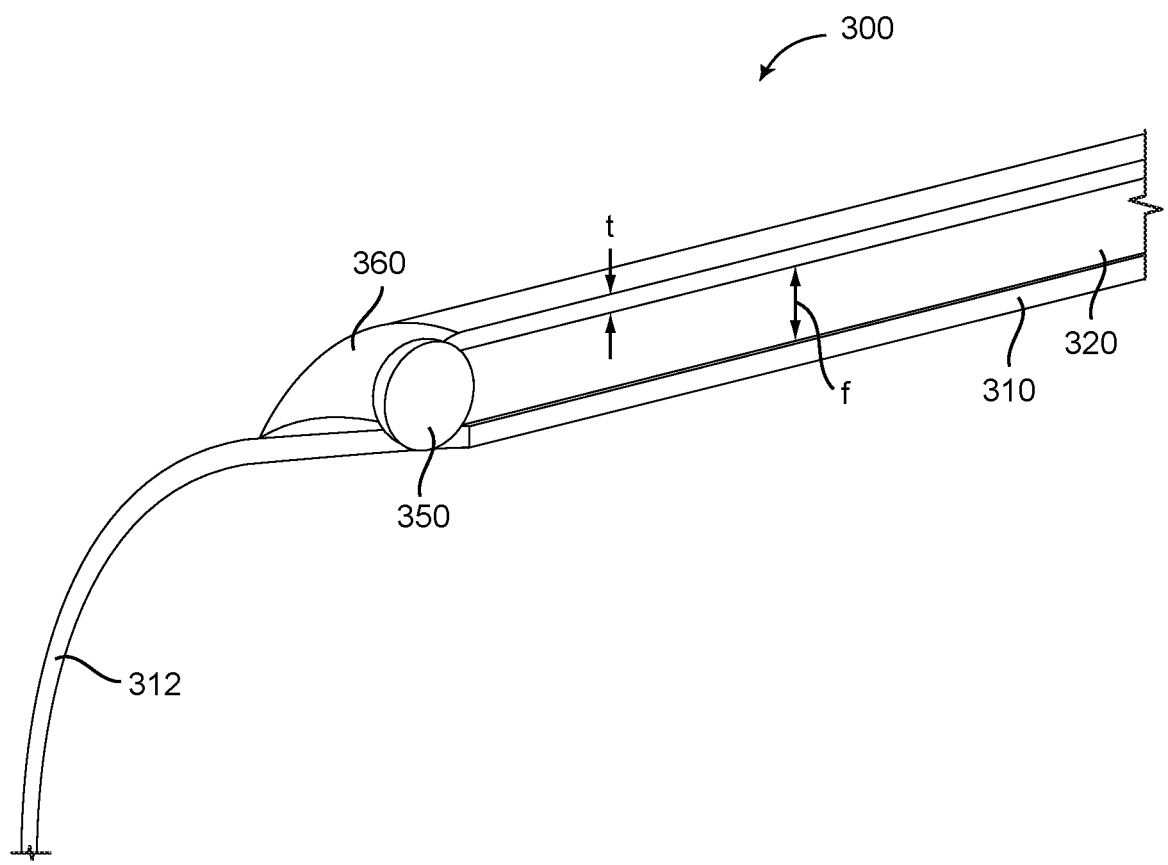
FIG. 6 is a perspective view of the distal end of the ophthalmic cannula assembly of FIG. 3, except longitudinally cut-away to show a cross-section of a fiber optic strand that is attached to the outer cannula surface.

FIG. 3 depicts an example hubbed ophthalmic cannula assembly 300. FIG. 4 is a perspective view of the distal end 312 of an ophthalmic cannula 310 of the hubbed ophthalmic cannula assembly 300. FIG. 5 is a plan view of the distal end 312 of the ophthalmic cannula 310 of the hubbed ophthalmic cannula assembly 300. FIG. 6 is a detailed perspective view of the distal end 312 of the hubbed ophthalmic cannula assembly 300, except longitudinally cut-away to show a cross-section of an optical fiber 320 that is attached to an outer surface of the ophthalmic cannula 310. In some implementations, the optical fiber 320 and the other optical fibers described herein may be a glass optical fiber. In some implementations, the optical fiber 320 and the other optical fibers described herein may be a strand of optical fibers. In other implementations, the optical fiber 320 and the other optical fibers described herein may be a single optical fiber.

The optical fiber 320 is operable to conduct light therethrough. The light conducted by the optical fiber 320 is emitted from the distal end of the optical fiber 320 to provide illumination to a surgical field. The light may be generated remotely from the optical fiber. For example, the optical fiber may be optically coupled to a light source that is remote from the ophthalmic cannula assembly 300. In some instances, the light source may be provided in a surgical console to which the optical fiber 320 is coupled directly or indirectly via an optical cable, for example. The various other optical fibers discussed herein may be similar to the optical fiber 320 and provide illumination to a surgical field.

Now referring to FIGS. 3-6, the ophthalmic cannula 310 of the ophthalmic cannula assembly 300 may have an outer cannula surface 315 and an inner cylindrical bore 316 that defines a longitudinal axis 302. The inner cylindrical bore 316 of the ophthalmic cannula 310 may define an inner radius r, and the ophthalmic cannula 310 may define an outer radius R and a cannula length L measured parallel to the longitudinal axis 302. In some implementations, the cannula length L may be in the range of 3 mm to 7 mm. However, the scope of the disclosure is not so limited. Rather, the length L of the ophthalmic cannula 310 may be any desired length.

In some implementations, the inner radius r of the inner cylindrical bore 316 may be in the range of 0.2 mm to 0.7 mm. However, the scope of the disclosure encompasses the inner radius r and the outer radius R being of any desired size.

A wall thickness of the ophthalmic cannula 310 between the inner cylindrical bore 316 and the outer cannula surface 315 may be determined by taking the difference of the outer radius R and the inner radius r. In some implementations, the wall thickness of the ophthalmic cannula 310 may be in the range of 10 microns to 60 microns. However, the scope of the disclosure is not so limited. Rather, a wall thickness of the ophthalmic cannula 310 may be any desired size.

Referring to FIGS. 3-6, a hub 330 may adjoin a proximal end 314 of the ophthalmic cannula 310. In some implementations, a maximum outer diameter D of the hub 330 may be larger than two times an outer diameter of the ophthalmic cannula 310, where the outer diameter of the ophthalmic cannula 310 is twice the outer radius R. In some implementations, the outer periphery of the hub 330 may include at least two gripping flats 332, for example to facilitate manipulation by a surgeon with tweezers. In some instances, the gripping flats 332 may be disposed parallel to each other on the periphery of the hub 330.

The optical fiber 320 may be attached to the outer surface 315 of the ophthalmic cannula 310 for at least a portion of the cannula length L. As shown in FIG. 6, the optical fiber 320 may define a fiber diameter f. In some instances, the fiber diameter f may be in the range of 20 microns to 60 microns. In other implementations, a fiber diameter f may be larger or smaller than the indicated range. Thus, the size of the fiber diameter f may be any desired size.

A cover material 360 may cover the optical fiber 320 for all or part of the length L of the ophthalmic cannula 310. In some implementations, a covered length of the optical fiber 320 may be in the range of 2 mm to 6 mm. In some implementations, a covered length of the optical fiber 320 may be the same portion of the length L of the ophthalmic cannula 310 to which the optical fiber 320 is attached thereto. However, in other instances, a length of the cover material 360 may be any desired length. Further, the cover material 360 may cover have gaps, such that the cover material 360 covers some portions of the optical fiber 320 while leaving one or more other portions of the optical fiber 320 uncovered.

In some instances, the cover material 360 may be an adhesive encapsulant that is adhered to and in contact with the outer cannula surface 315. As shown in FIG. 6, the cover material 360 may define a cover material thickness t that, in some instances, may be no greater than 50 microns over the optical fiber 320. However, the scope of the disclosure is not so limited. Rather, in other instances, the thickness t of the cover material may any desired thickness.

A light diffuser 350 may be adjoined to the optical fiber 320 at a distal tip of the optical fiber 320. In some instances, the light diffuser 350 may include a spherical bulge 351 at the distal tip of the optical fiber 320. As shown in FIG. 5, the light diffuser 350 may be longitudinally recessed from the distal end 312 of the ophthalmic cannula 310 by a diffuser recession distance b. In some instances, the diffuser recession distance b may be 0.5 mm or less, for example, to avoid the ophthalmic cannula 310 from blocking an amount of light emitted from the light diffuser 350. Light blocked by the ophthalmic cannula 310 may generate a shadow within the eye, reducing the effectiveness of the illumination. However, the scope of the disclosure is not so limited. Rather, the diffuser recession distance b may be any desired distance. Further in other instances, the diffuser recession distance b may be zero.

In some instances, an amount of light blocked by the ophthalmic cannula 310 may also be reduced or eliminated by introducing a notch 313 into the distal end 312 of the ophthalmic cannula 310. As shown in FIGS. 4 and 5, the distal end 312 of the ophthalmic cannula 310 may be longitudinally recessed at the location of the notch 313, and, in some instances, the light diffuser 350 may be circumferentially aligned with the notch 313.

Figure 20:
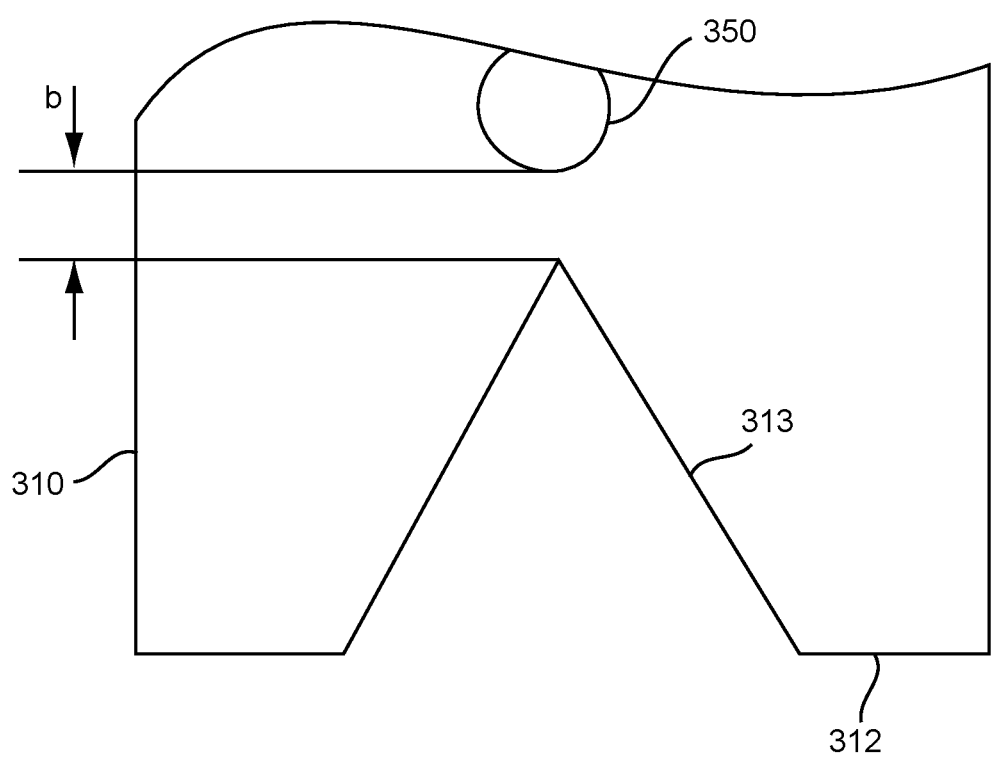
FIG. 20 is a detail view of an example ophthalmic cannula having a recess formed therein at a distal end of the ophthalmic cannula.

In some instances, the light diffuser 350 may be even further longitudinally recessed from the distal end 312 of the ophthalmic cannula 310, so that the light diffuser 350 also becomes longitudinally recessed with respect to the notch 313. In such implementations, as shown in FIG. 20, the desired diffuser recession distance b may be measured from the distal end 312 at the notch 313, rather than from the distal end 312 adjacent to the notch 313.

As shown in FIG. 6, the light diffuser 350 may not be within the length of the optical fiber 320 covered by the cover material 360 but, rather, may extend, partially or fully, distally beyond the cover material 360. The light diffuser 350 may extend beyond the cover material 360 in order to avoid excessive light attenuation, for example. In some instances, the light diffuser 350 may extend beyond the cover material 360 by a longitudinal spacing that may be 100 microns or less. In some instances, a distance between the distal tip of the light diffuser 350 and the distal tip of the cover material 360 may adequately protect the distal end of the glass fiber optic strand 320 from damage that might otherwise be caused by handling or insertion of the ophthalmic cannula 310 into the eye.

Figure 7:
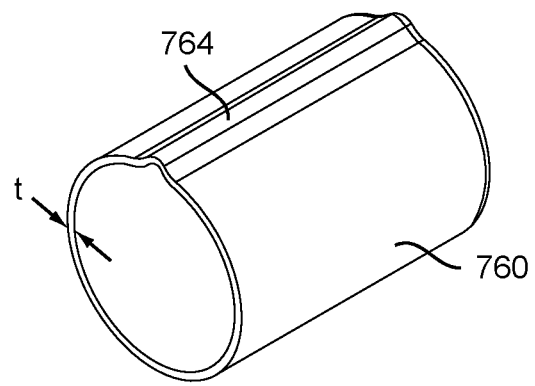
FIG. 7 is a perspective view of an example full sleeve to provide a cover material over a fiber optic strand on an outer cannula surface.

FIG. 7 is a perspective view of an example full sleeve 760 that fully wraps around or encircles an entire outer surface of an ophthalmic cannula, such as outer surface 315 of the ophthalmic cannula 310, and an optical fiber attached to the outer surface, such as the optical fiber 320, are fully covered by the full sleeve 760. The full sleeve 760 may help to protect the optical fiber from environmental disturbance or damage. In some implementations, the cover material forming the full sleeve 760 may be a polymer shrink wrap tube that wraps around the outer surface of an ophthalmic cannula. In such implementations, the full sleeve 760 may be shrunk onto the outer surface of the ophthalmic cannula in order to effectively and securely attach an optical fiber to the outer surface of an ophthalmic cannula. For example, in some instances, the full sleeve 760 may be secured to the outer surface of the ophthalmic cannula by heat shrinking the full sleeve 760. As shown in FIG. 7, the full sleeve 760 may include a longitudinally-oriented raised hump 764 to accommodate and conform to an underlying optical fiber. In other instances, the hump 764 may be omitted.

Figure 8:
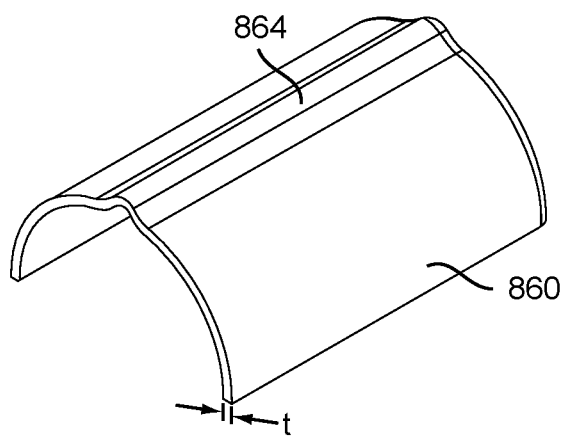
FIG. 8 is a perspective view of an example half sleeve to provide a cover material over a fiber optic strand on an outer cannula surface.

FIG. 8 is a perspective view of an example half sleeve 860 to cover an optical fiber disposed on an outer surface of an ophthalmic cannula. The half sleeve 860 may help to protect an optical fiber from environmental disturbance or damage. In the example shown in FIG. 8, the depicted cover material may be a polymer film that is adhered to the outer surface of an ophthalmic cannula. In such implementations, adhesion of the sleeve 860 may effectively and securely attach an optical fiber to the outer surface of an ophthalmic cannula. The sleeve 860 may include a longitudinally-oriented raised hump 864 to accommodate an underlying fiber optic strand while conforming and adhering to an underlying outer surface of an ophthalmic cannula. In other instances, the hump 864 may be omitted.

However, the scope of the disclosure is not so limited. Rather, in some implementations, a sleeve may extend circumferentially along the outer surface of an ophthalmic cannula less than 180 degrees. In other instances, a sleeve may extend circumferentially along an outer surface of an ophthalmic cannula more than 180 degrees but less than 360 degrees. Such a sleeve may also include a hump similar to hump 764 or 864, or such a hump may be omitted.

In some instances, the cover material of the sleeves 760 and 860 may each define a cover material thickness t that is 50 microns or less over an underlying optical fiber. However, the scope of the disclosure is not so limited. Rather, the thickness t of the cover material may be greater than 50 microns. Thus, the thickness t of the cover material may be any desired thickness.

Figure 9:
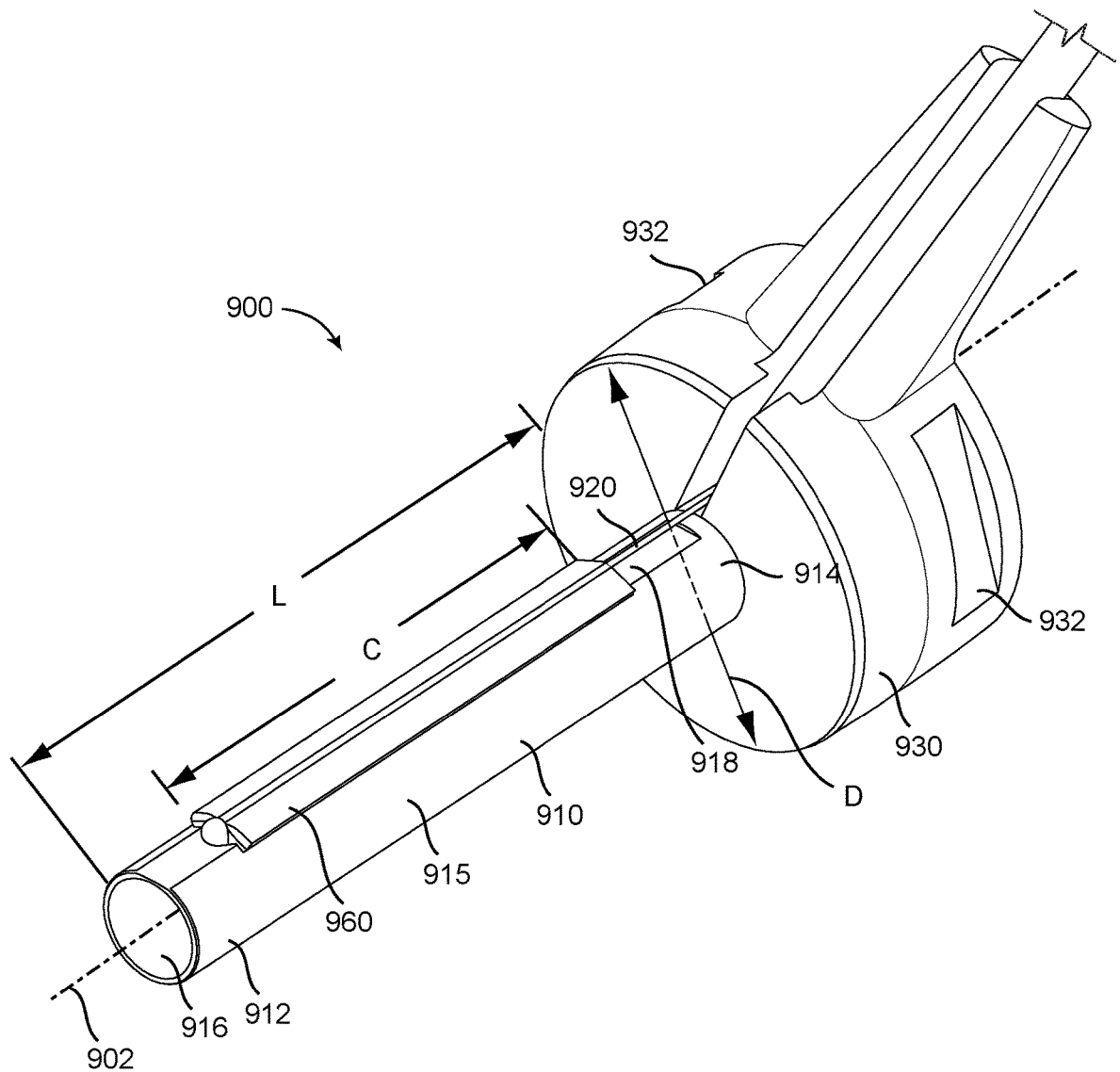
FIG. 9 depicts an example hubbed ophthalmic cannula assembly.
Figure 10:
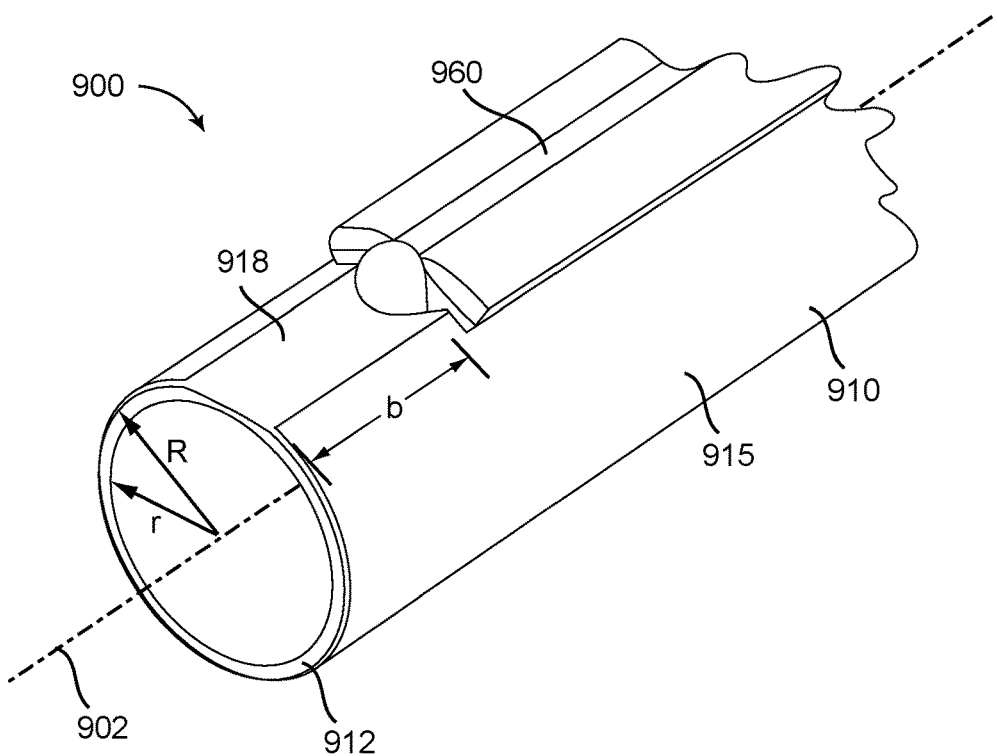
FIG. 10 is a perspective view of the ophthalmic cannula assembly of FIG. 9, near a distal end of the ophthalmic cannula assembly.
Figure 11:
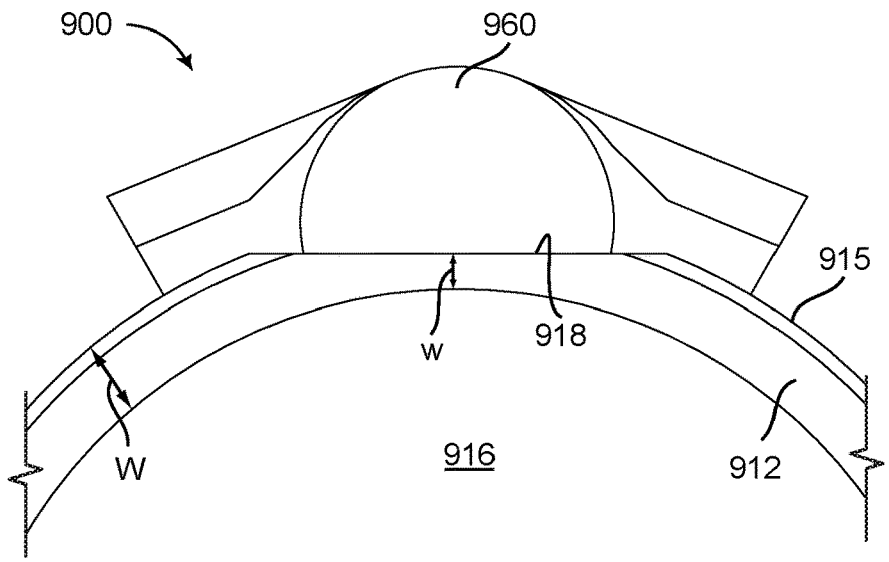
FIG. 11 is a distal end view of the ophthalmic cannula assembly of FIG. 9.
Figure 12:
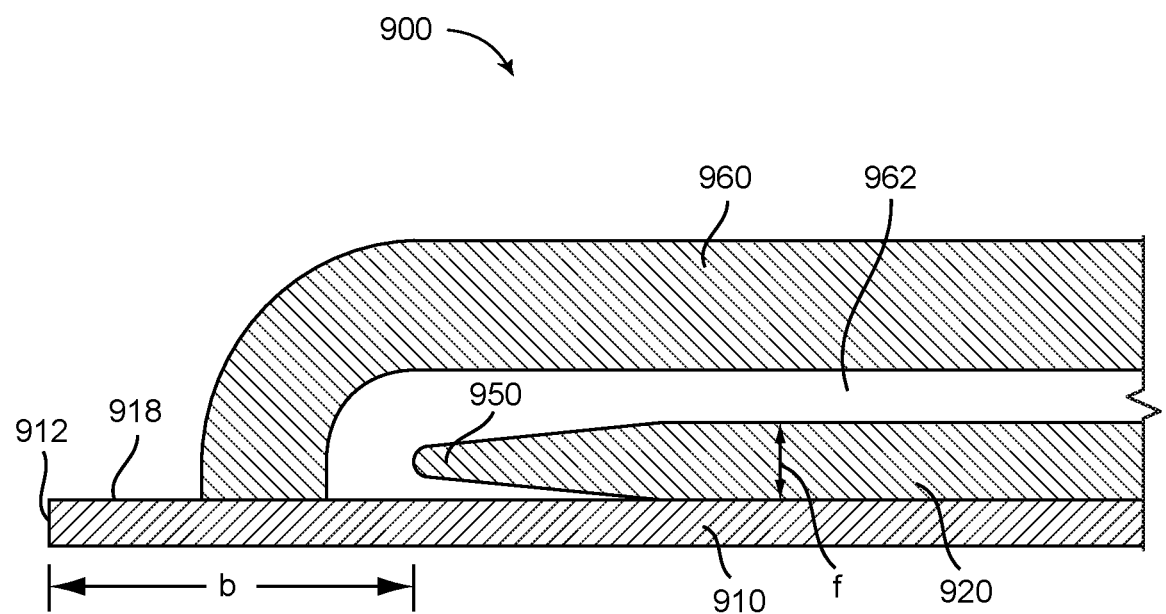
FIG. 12 depicts a longitudinal cross-section of the ophthalmic cannula assembly of FIG. 9, near a distal end of the ophthalmic cannula assembly.

FIG. 9 depicts an example hubbed ophthalmic cannula assembly 900. FIG. 10 is a perspective view of the ophthalmic cannula assembly 900 near its distal end 912. FIG. 11 is a distal end view of the ophthalmic cannula assembly 900. FIG. 12 depicts a longitudinal cross-section of the ophthalmic cannula assembly 900 near the distal end 912.

Now referring to FIGS. 9-12, an ophthalmic cannula 910 of the ophthalmic cannula assembly 900 may have an outer cannula surface 915 and an inner cylindrical bore 916 that defines a longitudinal axis 902. The inner cylindrical bore 916 of the ophthalmic cannula 910 may define an inner radius r, and the ophthalmic cannula 910 may define an outer radius R and a cannula length L measured parallel to the longitudinal axis 902. In some implementations, the cannula length L may be in the range of 3 mm to 7 mm. However, the scope of the disclosure is not so limited. Rather, the length L of the ophthalmic cannula 910 may be any desired length.

In some implementations, the inner radius r of the inner cylindrical bore 916 may be in the range of 0.2 mm to 0.7 mm. However, the scope of the disclosure encompasses the inner radius r and the outer radius R being of any desired size.

In certain embodiments, a wall thickness W of the ophthalmic cannula 910 between the inner cylindrical bore 916 and the outer cannula surface 915, which may be determined by a difference between the outer radius R and the inner radius r ($W=(R-r)$), may be in the range of 10 microns to 60 microns. However, the scope of the disclosure is not so limited. Rather, a wall thickness W of the ophthalmic cannula 910 may be any desired thickness.

A hub 930 may adjoin a proximal end 914 of the ophthalmic cannula 910. In some instances, a maximum outer diameter D of the hub 930 may be larger than two times an outer diameter of the ophthalmic cannula 910, where the outer diameter of the ophthalmic cannula 910 is twice the outer radius R. In some instances, the outer periphery of the hub 930 may include at least two gripping flats 932, for example to facilitate manipulation by a surgeon with tweezers. In some instances, the gripping flats 932 may be disposed parallel to each other on the periphery of the hub 930.

An optical fiber 920 is attached to the outer surface 915 of the ophthalmic cannula 910 for at least a portion of the cannula length L. As shown in FIG. 12, the optical fiber 920 may define a fiber diameter f. In some implementations, the fiber diameter f may be in the range of 20 microns to 60 microns. In other implementations, a fiber diameter f may be greater or smaller than the indicated range.

A cover material 960 may cover the optical fiber 920 for all or part of the length L of the ophthalmic cannula 910. In some instances, the covered length C of the optical fiber 920 may be in the range of 4 mm to 6 mm. In some implementations, the covered length C of the optical fiber 920 may be the same portion of the length L of the ophthalmic cannula 910 to which the glass fiber optic strand 920 is attached thereto. However, in other instances, a length of the cover material 960 may be any desired length. Further, the cover material 960 may cover have gaps, such that the cover material 960 covers some portions of the optical fiber 920 while leaving one or more other portions of the optical fiber 920 uncovered.

A distal end of the optical fiber 920 may terminate in a light diffuser 950, and the light diffuser 950 may be disposed within the covered length C of the optical fiber 920. In this way, the cover material 960 may help protect the light diffuser 950 and the distal end of the optical fiber 920 from damage that might otherwise be caused by handling or insertion of the ophthalmic cannula 910 into the eye.

In some implementations, the cover material 960 may be a transparent material that does not directly contact the light diffuser 950. Direct contact between the cover material 960 and the light diffuser 950 may be undesirable for performance of the light diffuser 950. In some implementations, the cover material 960 may be separated from the light diffuser 950 (and optionally also from the glass fiber optic strand 920) by a gap 962 such that the light diffuser 950 and the cover material 960 do not directly contact each other. The gap 962 may be filled with air or another gas.

As shown in FIG. 12, the light diffuser 950 may form distal tip at the distal end of the optical fiber 920. In other implementations, the light diffuser 950 may not be tapered. As shown in FIGS. 10 and 12, the light diffuser 950 may be longitudinally recessed from the distal end 912 of the ophthalmic cannula 910 by a diffuser recession distance b. In some instances, the diffuser recession distance b may be 0.5 mm or less, for example, to avoid excessive shadowing of the light by the ophthalmic cannula 910 itself. In other instances, the diffuser recession distance b may be greater than 0.5 mm. In still other instances, the diffuser recession distance b may be zero.

The outer cannula surface 915 may include a longitudinally-oriented flat 918. A wall thickness W of the cannula 910, circumferentially adjacent to the flat 918, may be greater than a wall thickness w of the cannula 910 within the longitudinal flat 918. The optical fiber 920 may be disposed on and attached to the longitudinal flat 918. The flat 918 may reduce the wall thickness of the cannula 910. For example, a reduction in wall thickness may be obtained by subtracting the wall thickness w from the wall thickness W. In some instances, this reduction in wall thickness may be in the range of 5 microns to 50 microns, for example, to accommodate all or a portion of the diameter f of the glass fiber optic strand 920. However, in other instances, this reduction in wall thickness may be greater or less than the indicated range.

Figure 13:
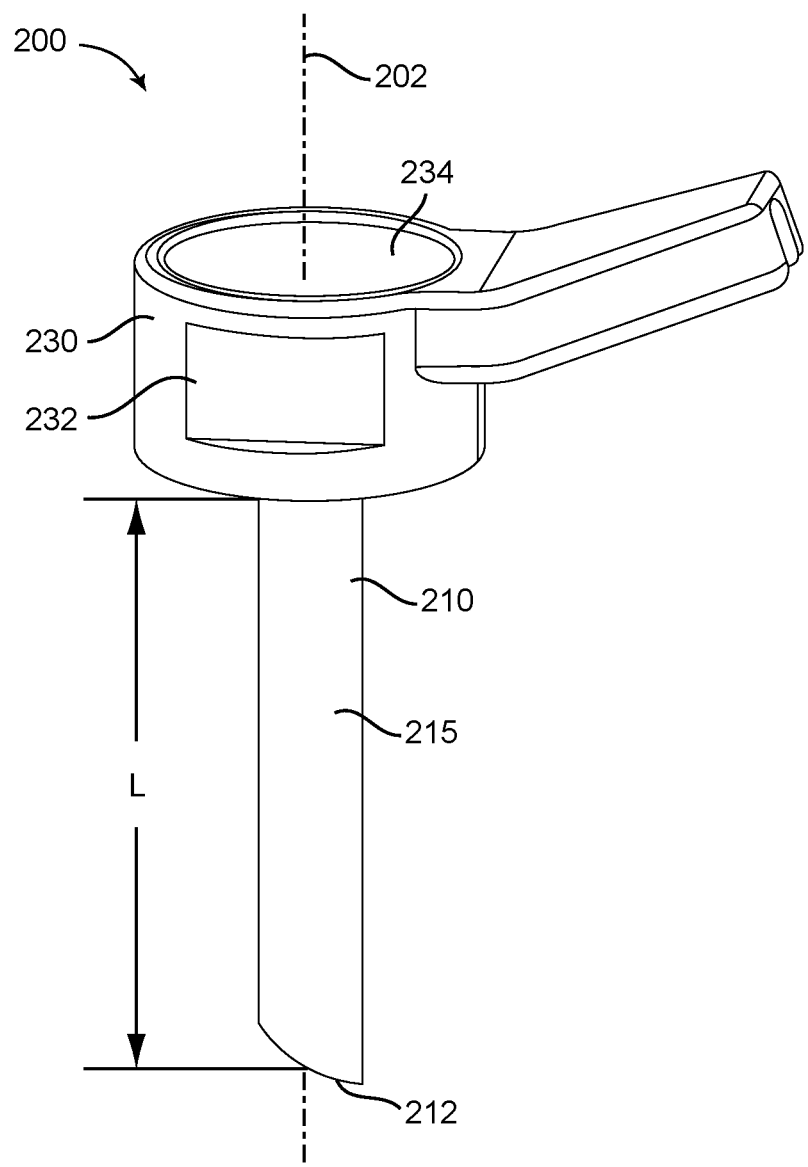
FIG. 13 is a side perspective view of an example hubbed ophthalmic cannula.
Figure 14:
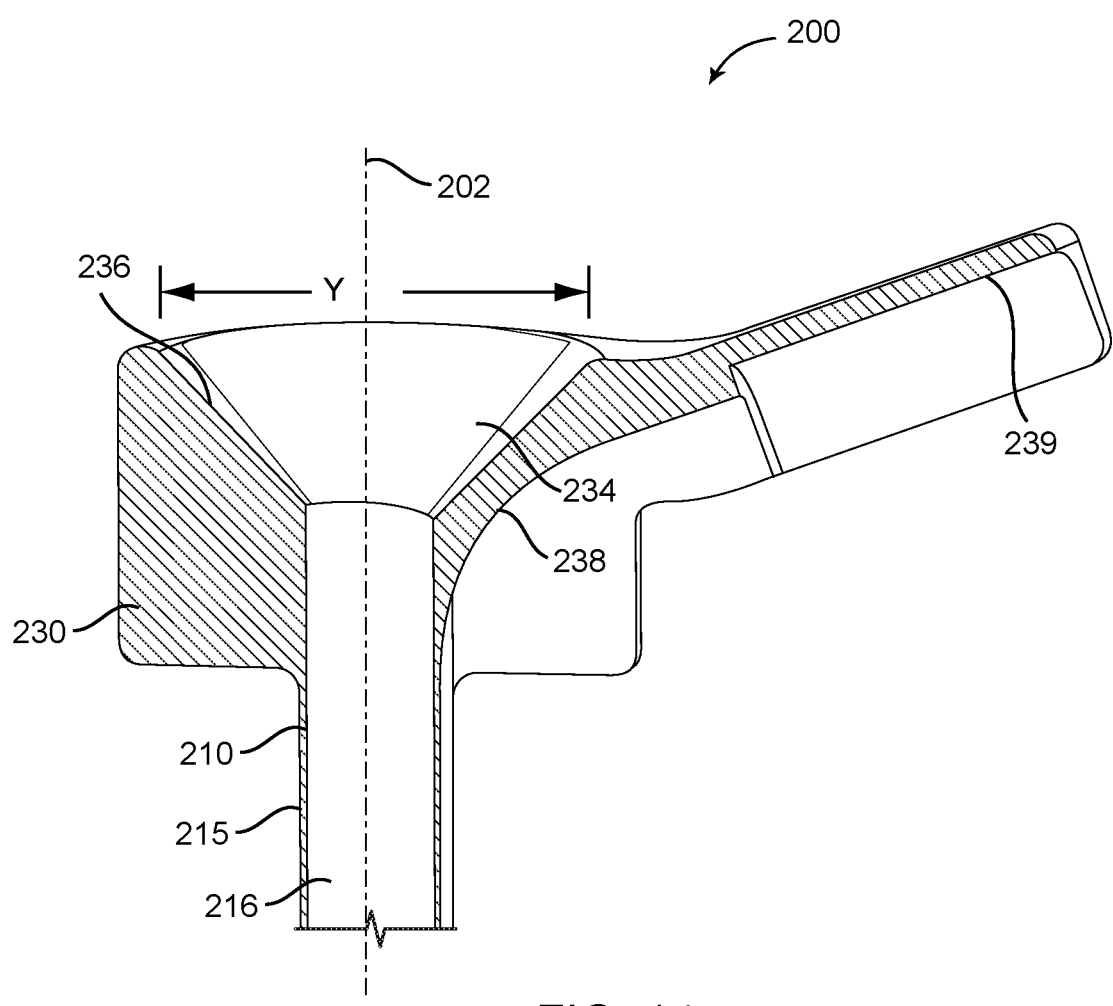
FIG. 14 is a cross-sectional view of an upper portion of the hubbed ophthalmic cannula of FIG. 13.
Figure 15:
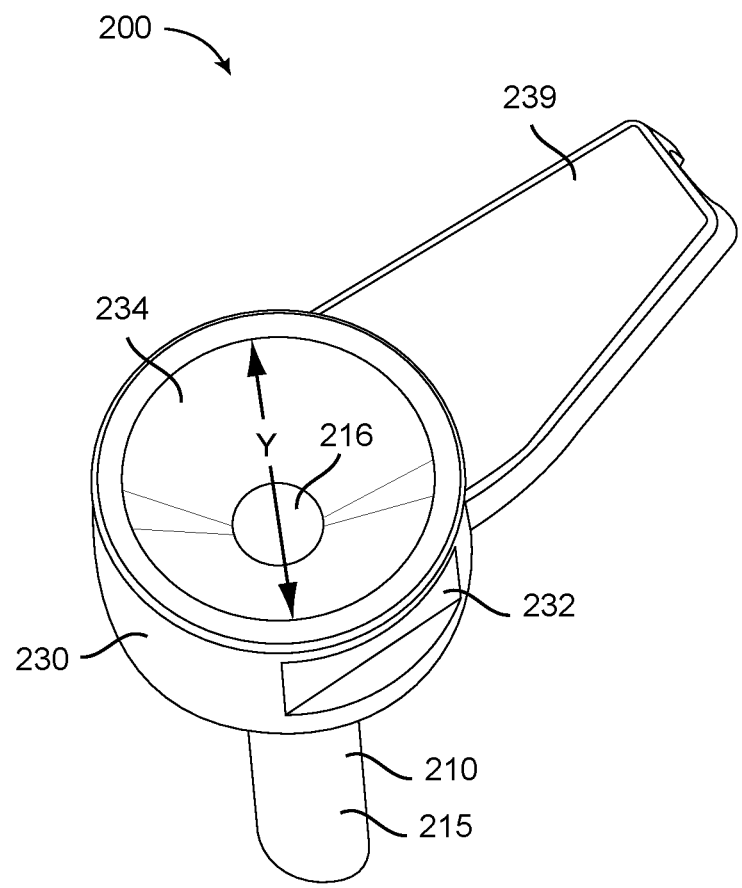
FIG. 15 is a top perspective view of the hubbed ophthalmic cannula of FIG. 13.
Figure 16:
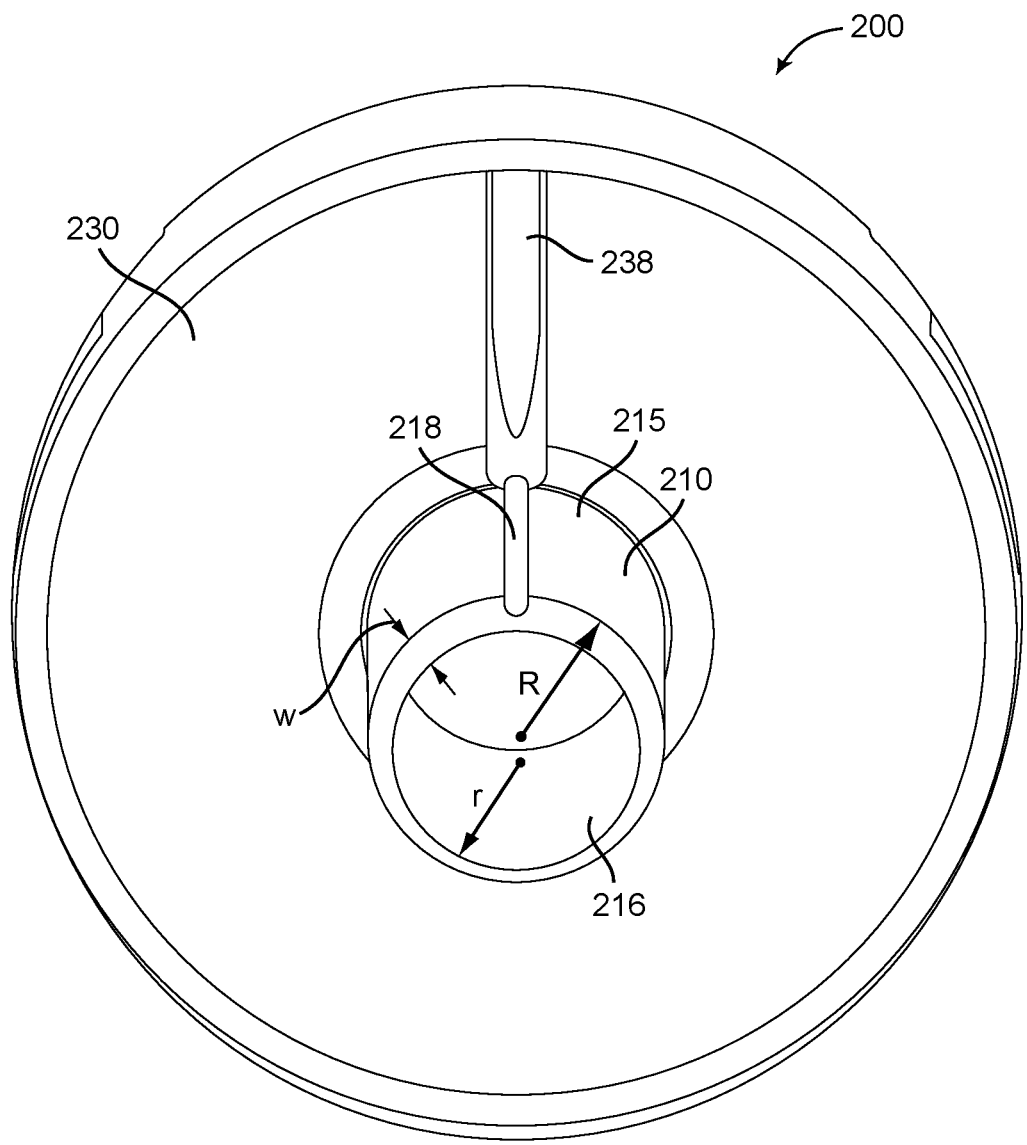
FIG. 16 is a bottom perspective view of the hubbed ophthalmic cannula of FIG. 13.

FIG. 13 is a side perspective view of an example hubbed ophthalmic cannula 200. FIG. 14 is a cross-sectional view of an upper region of the hubbed ophthalmic cannula 200. FIG. 15 is a top perspective view of the hubbed ophthalmic cannula 200. FIG. 16 is a bottom perspective view of the hubbed ophthalmic cannula 200.

Now referring to FIGS. 13-16, a cannula portion 210 of the hubbed ophthalmic cannula 200 may have an outer cannula surface 215 and an inner cylindrical bore 216 that defines a longitudinal axis 202. The inner cylindrical bore 216 of the hubbed ophthalmic cannula 200 may define an inner radius r, and the cannula portion 210 may define an outer radius R and a cannula length L measured parallel to the longitudinal axis 202. In some implementations, the cannula length L may be in the range of 3 mm to 7 mm. In some implementations, a distal end 212 of the cannula portion 210 may be canted to facilitate penetration into the tissue of the eye.

In some instances, the inner radius r of the inner cylindrical bore 216 may be in the range of 0.2 mm to 0.7 mm. In other instances, the inner radius r may be larger or smaller than the indicated range.

In some implementations, the inner cylindrical bore 216 may be eccentric with respect to the outer cannula surface 215, so that a wall thickness w, determined from a difference between the outer radius R and the inner radius r, of the cannula portion 210 varies around its circumference from a minimum wall thickness to a maximum wall thickness. In some implementations, the minimum wall thickness may be in the range of 10 microns to 60 microns. In other implementations, the minimum wall thickness may be larger or smaller than this range.

The hubbed ophthalmic cannula 200 includes a hub 230 adjoining the cannula portion 210. In some implementations, an outer periphery of the hub 230 may include one or more gripping flats 232. The gripping flats 232 may facilitate manipulation by a user with tweezers or another instrument. In some instances, the gripping flats 232 may be disposed parallel to each other on the hub 230. The hub 230 may also include a fiber guide 238 that includes an outer radial protrusion 239. As shown in FIGS. 13-16, the cannula portion 210 and the hub 230 may be a single monolithic component (e.g. a single injection-molded component) having material continuity. In other implementations, the cannula portion 210 and the hub 230 may be separate components coupled together.

The hub 230 may include a funnel opening 234 therethrough that leads to and is contiguous with the inner cylindrical bore 216 of the cannula portion 210. The funnel opening 234 is operable to guide surgical instruments into the inner cylindrical bore 216 of the cannula portion 210. The funnel opening 234 may include an interior chamfer 236 that gives the funnel opening a maximum opening diameter Y that, in some implementations, may be greater than twice the inner radius r of the inner cylindrical bore 216 of the cannula portion 210.

The outer cannula surface 215 may include a longitudinal groove 218 that may be disposed circumferentially adjacent to where the wall thickness w of the cannula portion 210 is a maximum. Because the longitudinal groove 218 has a finite depth, the wall thickness w of the cannula portion 210 circumferentially adjacent to the longitudinal groove 218, is greater than the wall thickness w of the cannula portion 210 within the longitudinal groove 218. The longitudinal groove 218 may be dimensioned to at least partially receive an optical fiber so that the optical fiber can be disposed at least partially within the longitudinal groove 218 along at least a portion of the cannula length L. In some instances, the longitudinal groove 218 may have a groove depth in the range of 5 microns to 50 microns. In other instances, a groove depth of the longitudinal groove 218 may be larger or smaller than the indicated range. Thus, the groove depth may be any desired depth.

Figure 17:
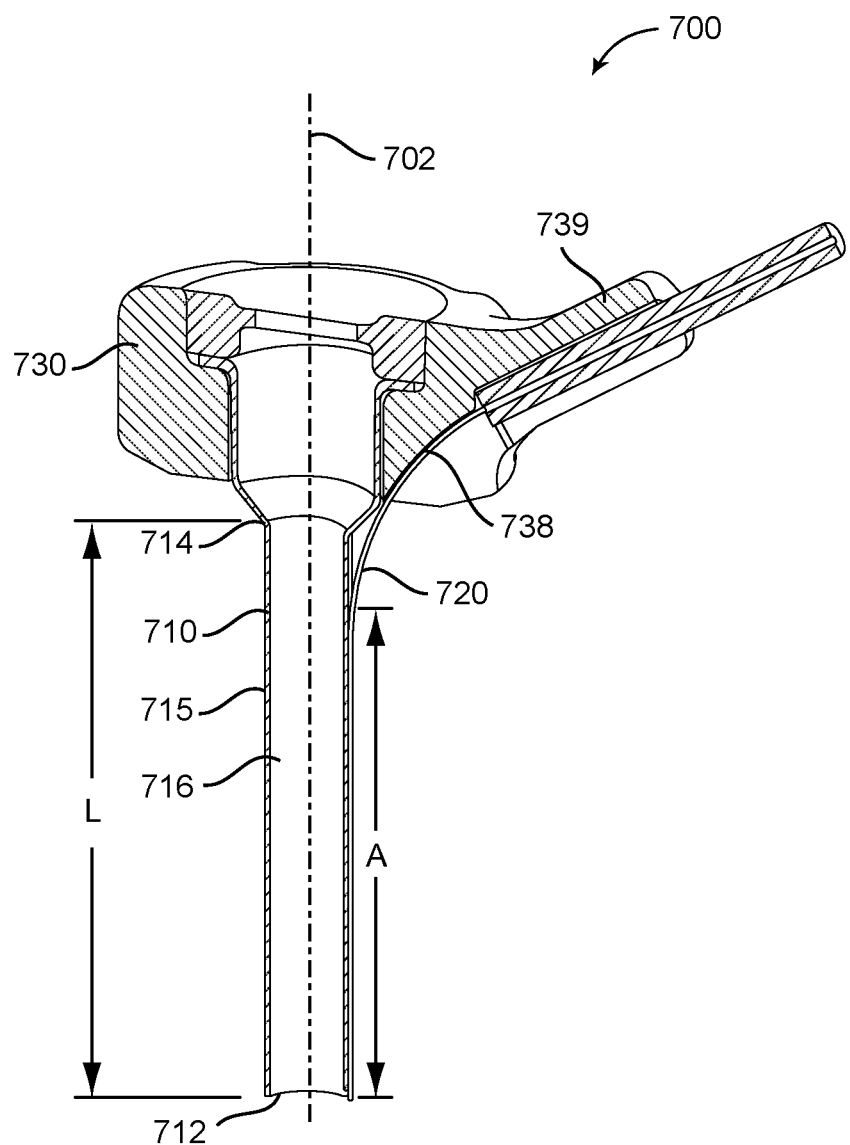
FIG. 17 depicts a longitudinal cross-section of an example hubbed ophthalmic cannula.

FIG. 17 depicts a longitudinal cross-section of an example hubbed ophthalmic cannula assembly 700. The hubbed ophthalmic cannula assembly 700 includes a cannula 710 having an outer cannula surface 715 and an inner cylindrical bore 716 that defines a longitudinal axis 702.

In some implementations, the cannula 710 may be formed of stainless steel. A wall thickness of the cannula 710 may be in the range of 10 microns to 60 microns. In other implementations, a wall thickness of the cannula 710 may be greater or smaller than the indicated range. Thus, the wall thickness of the cannula 710 may be any desired thickness.

Referring to FIG. 17, an optical fiber 720 may be attached to the outer surface 715 of the cannula 710 for an attached length A of the cannula length L. In some instances, a cover material, such as a cover material similar to the sleeve 760 of FIG. 7, the sleeve 860 of FIG. 8, or another sleeve described herein, may cover the optical fiber 720 for all or part of the attached length A and may serve to attach the optical fiber 720 to the outer surface 715 of the cannula 710. In some implementations, the cannula length L may be in the range of 3 mm to 7 mm, and the attached length A may be in the range of 2 mm to 6 mm. In other instances, the cannula length L may be larger or smaller than the indicated range. Thus, the cannula length L may be any desired length. Further, the attached length A may be larger or smaller than the indicated range. Thus, the attached length A may be any desired length.

A hub 730 may adjoin a proximal end 714 of the cannula 710. For example, in some implementations, the cannula 710 may be fabricated of extruded metal and pressed into a bore in the hub 730. In some instances, the hub 730 may be fabricated of injection molded plastic. The hub 730 may include a fiber guide 738 that includes an outer radial protrusion 739. As shown in FIG. 17, the optical fiber 720 may be bent further away from the longitudinal axis 702 by the fiber guide 738, with the optical fiber 720 being disposed closest to the longitudinal axis 702 along the attached portion A of the cannula length L.

The optical fiber 720 may include a light diffuser at its distal end, adjacent to the distal end 712 of the cannula 710. For example, in some implementations, the light diffuser may include a spherical bulge or have a tapered shape at the distal tip of the optical fiber 720, as described with reference to other figures herein.

Figure 18:
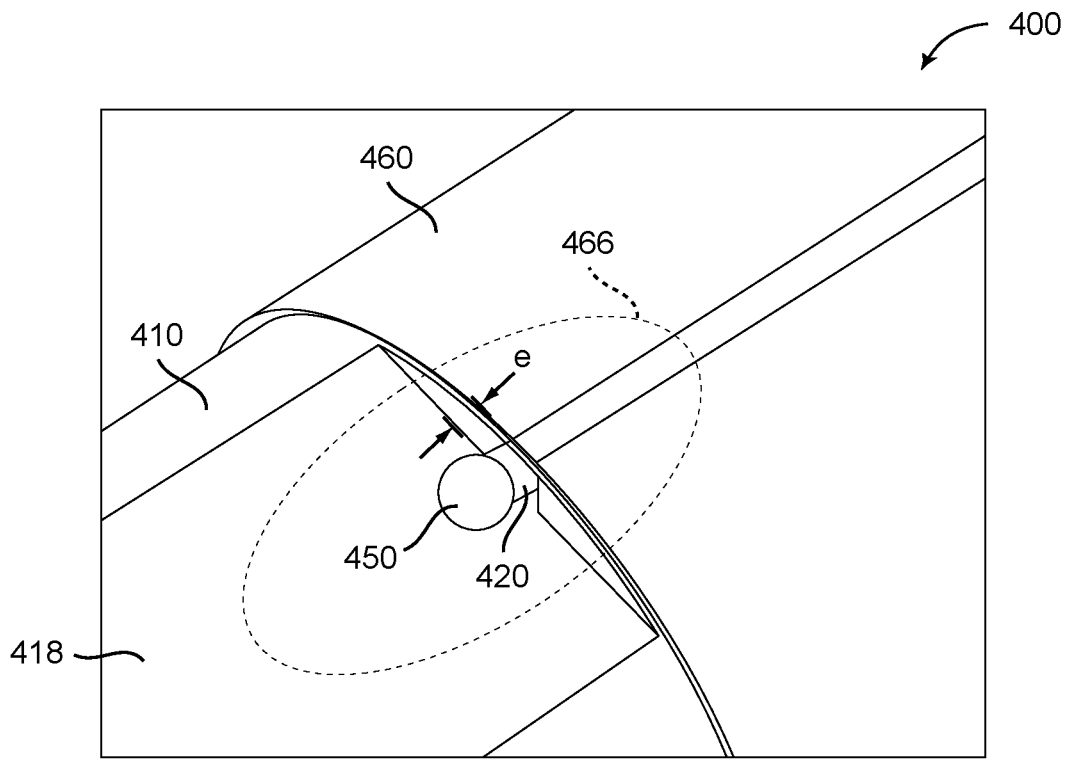
FIG. 18 depicts an example encapsulated light diffuser at the distal end of an ophthalmic cannula assembly.

FIG. 18 is close-up view of a distal region of an example ophthalmic cannula assembly 400. The ophthalmic cannula assembly 400 includes an optical fiber 420 attached to an outer surface of a cannula 410. In some instances, the optical fiber 420 may be attached along a longitudinally-oriented flat 418. A light diffuser 450 may be adjoined to a distal end of the optical fiber 420. In the example of FIG. 18, the light diffuser 450 may include a spherical bulge at the distal tip of the optical fiber 420. The light diffuser 450 may be longitudinally recessed from the distal end of the cannula 410, for example, to help protect the light diffuser 450 and the optical fiber 420 during insertion of the cannula 410 into the tissue of the eye.

A cover material 460 may protect and affix the optical fiber 420 to the cannula 410 at the flat 418. In some instances, the light diffuser 450 may be positioned outside of the cover material 460. Thus, in some implementations, the light diffuser 450 may extend distally beyond the cover material 460, for example, to avoid excessive light attenuation. In some implementations, the light diffuser 450 may extend beyond the cover material 460 by a longitudinal spacing e that may be 100 microns or less. A longitudinal spacing e within this range may adequately protect the distal end of the glass fiber optic strand 420 from damage that might otherwise be caused by handling or insertion of the cannula 410 into the eye. However, the scope of the disclosure is not so limited. Rather, the longitudinal spacing e may be greater than 100 microns. In still other implementations, the longitudinal spacing e may be zero.

The ophthalmic cannula assembly 400 may further include a transparent or translucent encapsulate bead 466 disposed over and in contact with the light diffuser 450, for example to further protect the light diffuser 450 or the optical fiber 420 from damage that might otherwise be caused by handling or insertion of the cannula 410 into the eye. In some implementations, the encapsulate bead 466 may include particles incorporated therein to create a refractive index gradient to further diffuse the emitted light.

Figure 19:
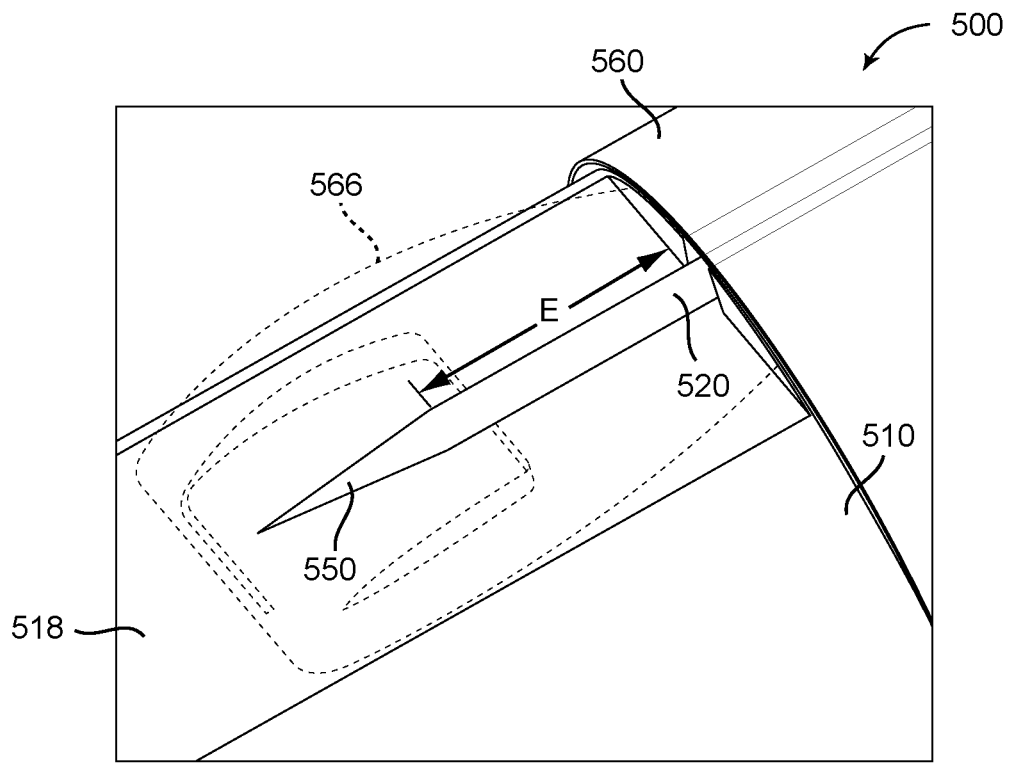
FIG. 19 depicts an example encapsulated light diffuser at the distal end of an ophthalmic cannula assembly.

FIG. 19 is close-up view of a distal region of an example ophthalmic cannula assembly 500. The ophthalmic cannula assembly 500 includes an optical fiber 520 attached to an outer surface of a cannula 510. The optical fiber 520 may be attached to the outer surface of the cannula 510 at a longitudinally-oriented flat 518. A light diffuser 550 may be adjoined to a distal end of the optical fiber 520. As shown in FIG. 19, the light diffuser 550 may have a tapered shape that defines a tapered distal tip of the optical fiber 520. The light diffuser 550 may be longitudinally recessed from the distal end of the ophthalmic cannula 510, for example, to help protect the light diffuser 550 and the optical fiber 520 during insertion of the cannula 510 into the tissue of the eye.

A cover material 560 may be included to help protect and affix the optical fiber 520 to the cannula 510 along the longitudinally-oriented flat 518. The light diffuser 550 may be disposed distally of and not covered by the cover material 560. Rather, the light diffuser 550 may extend distally beyond the cover material 560, for example, to avoid excessive light attenuation. In some implementations, the light diffuser 550 may extend beyond the cover material 560 by a longitudinal spacing E that may be 100 microns or less. A longitudinal spacing E within this range may adequately protect the distal end of the optical fiber 520 from damage that might otherwise be caused by handling or insertion of the ophthalmic cannula 510 into the eye.

The ophthalmic cannula assembly 500 may further include a transparent or translucent encapsulate bead 566 disposed over and in contact with the light diffuser 550. The encapsulate bead 566 may protect the light diffuser 550 or the optical fiber 520 from damage that might otherwise be caused by handling or insertion of the ophthalmic cannula 510 into the eye. In some implementations, the encapsulate bead 566 may include particles incorporated therein to create a refractive index gradient to further diffuse the emitted light.

Incorporation of an optical fiber into an ophthalmic cannula assembly as described herein reduces the number of probes that are simultaneously extending into the eye during an ophthalmic surgical procedure. The reduction in probes present in the eye during a surgical procedure reduces the number of probes that must be manipulated by a user, such as a surgeon, and provides more room near the eye for the surgeon to perform the surgical procedures. Further, fewer probes extending simultaneously into an eye during ophthalmic surgery may reduce the time required to perform the surgical procedure, may reduce trauma to the eye, and may reduce the risk infection to the eye as a result of few entry wounds into the eye.

In the foregoing specification, the disclosure is provided with reference to specific examples, but those skilled in the art will recognize that the disclosure is not limited to those. One or more of these examples may reduce the number of required probes, incision points, or cannulae through the surface of the eye during ophthalmic surgery.

It is contemplated that various features and aspects of the disclosure may be used individually or jointly and possibly in a different environment or application. For example, although the present disclosure was made in the context of ophthalmology, the substance of the present disclosure may be applicable to fields outside of ophthalmology. The specification and drawings are, accordingly, to be regarded as illustrative and exemplary rather than restrictive. For example, the word "preferably," and the phrase "preferably but not necessarily," are used synonymously herein to consistently include the meaning of "not necessarily" or optionally. "Comprising," "including," and "having," are intended to be open-ended terms.

What is claimed is:

1. An ophthalmic cannula assembly comprising:
   a cannula including an outer cannula surface and an inner cylindrical bore that defines a longitudinal axis and an inner radius, the cannula defining a cannula length measured parallel to the longitudinal axis;
   a hub adjoining a proximal end of the cannula, the cannula and hub configured to be received onto a trocar piercing device to be inserted into an eye and further configured to hold an incision, created by the trocar piercing device during the insertion process, open during an ophthalmic procedure to allow repeated removal and insertion of instruments through the incision;
   an optical fiber attached to the outer cannula surface for at least a portion of the cannula length;

a cover material that covers at least a portion of the optical fiber and that is in contact with the outer cannula surface; and a light diffuser at a distal tip of the optical fiber.

2. The ophthalmic cannula assembly of claim 1 wherein the cover material is an adhesive encapsulant that is adhered to the outer cannula surface.

3. The ophthalmic cannula assembly of claim 1 wherein the cover material is one of a polymer shrink wrap tube that wraps around the outer cannula surface or a polymer film that is adhered to the outer cannula surface.

4. The ophthalmic cannula assembly of claim 1 wherein the light diffuser comprises a spherical bulge at the distal tip of the optical fiber.

5. The ophthalmic cannula assembly of claim 1 wherein at least a portion of the light diffuser comprises a tapered shape.

6. The ophthalmic cannula assembly of claim 1 wherein a length of the optical fiber covered by the cover material is the same as a length of the optical fiber attached portion of the cannula.

7. The ophthalmic cannula assembly of claim 1 wherein the light diffuser is uncovered by the cover material, and wherein a longitudinal spacing between the light diffuser and the cover material is no greater than 100 microns.

8. The ophthalmic cannula assembly of claim 1 wherein the cover material is a transparent material, wherein the light diffuser is covered by the cover material, and wherein the light diffuser is not in direct contact with the cover material.

9. The ophthalmic cannula assembly of claim 1 wherein the hub comprises a funnel opening therethrough, wherein the funnel opening extends to and is contiguous with the inner cylindrical bore of the cannula, the funnel opening comprising an interior chamfer defining a maximum opening diameter that is greater than twice an inner diameter of the inner cylindrical bore of the cannula.

10. The ophthalmic cannula assembly of claim 1 wherein a wall thickness of the cannula, between the inner cylindrical bore and the outer cannula surface, is in the range of 10 microns to 60 microns.

11. The ophthalmic cannula assembly of claim 1 wherein the outer cannula surface includes a longitudinal groove, and a wall thickness of the cannula circumferentially adjacent to the longitudinal groove is greater than the wall thickness of the cannula within the longitudinal groove, and wherein the optical fiber is disposed at least partially within the longitudinal groove.

12. The ophthalmic cannula assembly of claim 11 wherein the longitudinal groove has a groove depth in the range of 5 microns to 50 microns.

13. The ophthalmic cannula assembly of claim 11 wherein the inner cylindrical bore is eccentric with respect to the outer cannula surface, so that the wall thickness of the cannula varies around a circumference of the cannula from a minimum wall thickness to a maximum wall thickness, and wherein the longitudinal groove is disposed circumferentially adjacent to the maximum wall thickness.

14. The ophthalmic cannula assembly of claim 1 further comprising a flat that extends longitudinally on the outer cannula surface, and a wall thickness of the cannula circumferentially adjacent to the flat is greater than the wall thickness of the cannula at the flat, and wherein the optical fiber is disposed at least partially on the flat.

15. The ophthalmic cannula assembly of claim 1 wherein the light diffuser is longitudinally recessed from a distal end of the cannula by a diffuser recession distance that is no greater than 0.5 mm (millimeters).

16. The ophthalmic cannula assembly of claim 1 wherein a distal end of the cannula includes a notch where the distal end of the cannula is longitudinally recessed, and wherein the light diffuser is circumferentially aligned with the notch.

17. The ophthalmic cannula assembly of claim 16 wherein the light diffuser is longitudinally recessed from the notch by a diffuser recession distance that is no greater than 0.5 mm.

18. The ophthalmic cannula assembly of claim 1 wherein the cannula and the hub are a single monolithic component having material continuity.

19. The ophthalmic cannula assembly of claim 1 wherein the hub comprises a fiber guide that includes an outer radial protrusion, and wherein the optical fiber is bent further away from the longitudinal axis by the fiber guide, a distance between the optical fiber and the longitudinal axis being smallest at a location where the optical fiber is attached to the outer cannula surface.

20. The ophthalmic cannula assembly of claim 1 wherein an outer periphery of the hub includes at least two gripping flats.

* * * * *